United States Patent [19]
Caldwell et al.

[11] Patent Number: 5,240,618
[45] Date of Patent: Aug. 31, 1993

[54] ELECTRICAL FIELD-FLOW FRACTIONATION USING REDOX COUPLE ADDED TO CARRIER FLUID

[75] Inventors: Karin D. Caldwell; Yu-Shu Gao, both of Salt Lake City, Utah

[73] Assignee: University of Utah Research Foundation, Salt Lake City, Utah

[21] Appl. No.: 829,970

[22] Filed: Feb. 3, 1992

[51] Int. Cl.$^5$ ............................................. B01D 17/00
[52] U.S. Cl. .................... 210/748; 73/61.71; 204/153.1; 209/127.1; 209/155; 210/757; 210/758
[58] Field of Search ............ 210/243, 511, 748, 198.2, 210/757, 758; 204/180.1, 299 R, 153.1, 186; 209/1, 155, 127.1, 129, 131; 73/61.71

[56] References Cited

U.S. PATENT DOCUMENTS

| | | | |
|---|---|---|---|
| 3,393,801 | 7/1968 | Gustavsson | 73/61.71 |
| 3,449,938 | 6/1969 | Giddings | 210/198.2 |
| 4,214,981 | 7/1980 | Giddings | 210/748 |
| 4,440,638 | 4/1984 | Judy et al. | 210/748 |
| 4,704,353 | 11/1987 | Humphries et al. | 204/153.1 |
| 4,874,507 | 10/1989 | Whitlock | 204/180.1 |
| 4,963,815 | 10/1990 | Hafeman | 204/153.1 |
| 5,039,426 | 8/1991 | Giddings | 210/243 |
| 5,064,515 | 11/1991 | Harapanahalli | 210/748 |
| 5,122,246 | 6/1992 | Schmidt et al. | 204/180.1 |

FOREIGN PATENT DOCUMENTS

| | | | |
|---|---|---|---|
| 833555 | 5/1981 | U.S.S.R. | 210/748 |

*Primary Examiner*—Joseph W. Drodge
*Attorney, Agent, or Firm*—Terry M. Crellin

[57] ABSTRACT

Improved apparatus and procedures for electrical field-flow fractionation is disclosed. A test sample is injected into the liquid carrier stream flowing through the flow channel of the apparatus. The apparatus comprises a thin flow channel having a top, a bottom, and two side walls, with a fluid carrier inlet at one end and an outlet at the other end. The top and bottom walls are formed such that at least the inner surfaces thereof that face the flow channel are made of an electrically conductive material so that the inner surfaces thereof form electrodes as well as opposite, broad boundary surfaces of the flow channel. A voltage differential is applied to the electrically conductive inner surfaces of the top and bottom walls. The carrier fluid flowing through the channel can be deionized or distilled water as well as water containing a red-ox couple such as quinone/hydroquinone.

8 Claims, 1 Drawing Sheet

ELECTRICAL FIELD-FLOW FRACTIONATION USING REDOX COUPLE ADDED TO CARRIER FLUID

BACKGROUND OF THE INVENTION

1. Government Support

This invention was made with Government support under Public Health Service Grant GM38008-03 awarded by the National Institutes of Health. The Government has certain rights in the invention.

2. Field of the Invention

The present invention relates to procedures for resolution and separation of particles in a test sample using field flow fractionation techniques. In particular, the present invention relates to novel apparatus and procedures in electrical field strength mode of field flow fractionation.

3. State of the Art

The concept of field flow fractionation was introduced in the 1960's and has been developed into an effective tool for the separation and analysis of macromolecules, polymers, colloids and other fine particles. Many improvements in the basic field flow fractionation process have been suggested in the prior art.

Field-flow fractionation consists of a great number of operating modes and subtechniques, each having its own unique characteristics and range of applicability. It has been suggested in many of the prior art patents issued in the field of field-flow fractionation that an electrical field can be one of the field forces used to operate on the particles as they pass through the channel of the field-flow fractionation apparatus. In only one of the prior art patents is there any suggestion of a particular arrangement of the electrodes that produce the electrical field.

In U.S. Pat. No. 4,440,638, issued on Apr. 3, 1984, there is disclosed a surface field-effect device for manipulation of charged species. The apparatus disclosed in U.S. Pat. No. 4,440,638 includes a channel in which the fluid flowing therethrough is in physical contact at one side of the channel with a control electrode made of metal. On the opposite side of the channel, the fluid is in contact with a dielectric layer that overlies the other electrode. Only one of the electrodes of the pair of electrodes is in contact with the fluid flowing through the channel.

Since the first implementation of electrical field-flow fractionation in 1971, the electrical field has almost universally been applied by electrodes positioned external to semipermeable membranes that form the opposite broad sides of the flow channel. This arrangement was necessary to minimize polarization products that are produced at electrodes that are in contact with the fluid flowing in the channel. Even using electrodes positioned external to semipermeable membranes has been hampered by the problem of polarization.

Unfortunately, despite the many attractive features offered by electrical field forces in field-flow fractionation, the application of such processes has so far met only limited success. Although differential migration of proteins with different isoelectric points was demonstrated early on, the inherently large retention range of electrical field-flow fractionation was never realized because of the detrimental polarization occurring at the electrodes. The original flow channels with their semipermeable membrane walls were difficult to maintain in a parallel plate configuration, and polarization at the membrane surfaces was always a potential problem as was the potential for electroosmotic flow.

4. Objectives

A principal objective of the invention is to provide novel apparatus and improved procedures for separation and resolution of particles in test samples using field-flow fractionation techniques.

A further objective of the present invention is to provide a simple and effective flow apparatus for electrical field-flow fractionation processes, wherein the flow apparatus comprises a channel having superior structural rigidity, with the electrodes of the apparatus being incorporated into the surface of the rigid wall members of the flow channel.

An additional objective of the present invention is to provide novel apparatus and procedures for electrical field-flow processes in which polarization at the electrodes is maintained at an acceptable low level and relatively high field strengths are achieved at low voltage differentials between the electrodes.

It is still a further objective of the present invention to provide apparatus and procedures for electrical field-flow processes that achieve consistently high resolution and particle separation that has not been achievable with apparatus and procedures of the prior art.

BRIEF DESCRIPTION OF THE INVENTION

The above objectives are achieved in accordance with the present invention by providing an improved system for electrical field-flow fractionation. In the new system, novel apparatus and procedures are used, with the flow channel of the field-flow fractionation system being constructed so that the electrical field is applied to the inner surfaces of opposite, broad side walls of the flow channel rather than to electrodes placed outside the confinement of the flow channel. This allows the flow channel to be made of rigid materials having structural stability whereby the flow channel can be constructed to precision dimensions with a high degree of uniformity in the channel construction. In a preferred embodiment of the novel flow channel construction of the present invention, the electrodes are formed of an electrically conductive, rigid material that also forms the opposite, broad side walls of the flow channel.

The normal carrier buffers used in electrical field-flow fractionation processes of the prior art were found to be totally unusable when flow channels are used in which the electrodes serve as opposite side walls of the flow channel. The normal carrier buffers, such as 0.01M Tris-HCl, result in almost instantaneous polarization of the electrodes forming the walls of the flow channel. Polarization of the electrodes causes the electrodes to act as a capacitor and thereby greatly reduce passage of current through the channel regardless of voltage applied to the electrodes. Reduction in current results in a detrimental reduction in the strength of the working field applied to the flow channel, whereby the apparatus becomes essentially useless.

Additional objects and features of the invention will become apparent from the following detailed description, taken together with the accompanying drawings.

THE DRAWINGS

FIG. 1 is an exploded, pictorial representation of a preferred embodiment of flow channel apparatus in accordance with the present invention; and FIG. 2 is an exploded, pictorial representation similar to that of FIG. 1 but showing a modified embodiment of the flow channel apparatus.

DETAILED DESCRIPTION OF THE PREFERRED EMBODIMENTS

Figure 1:
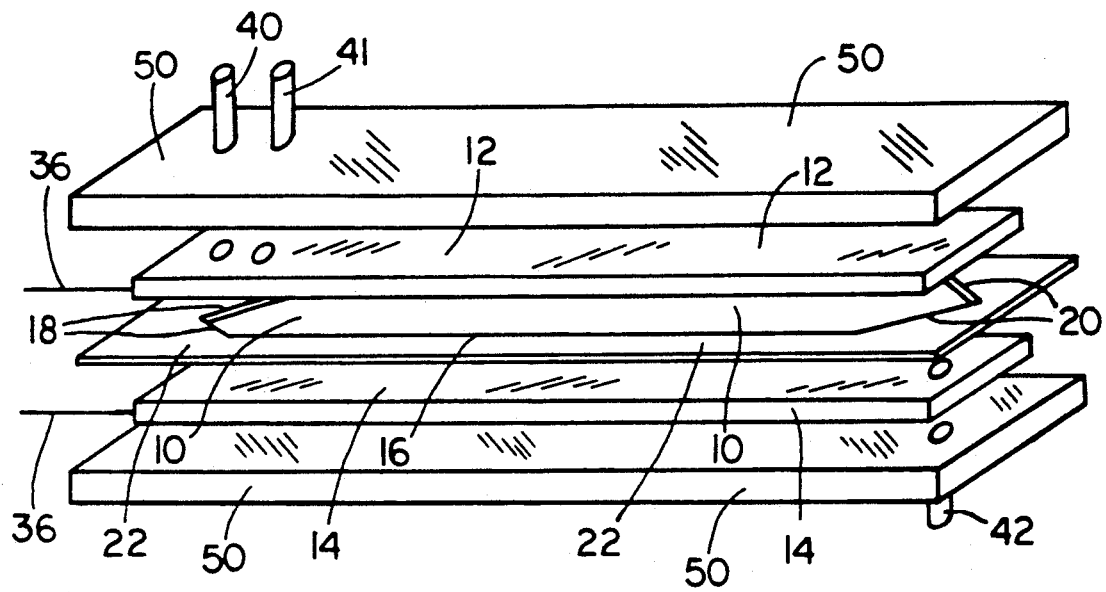

In field flow fractionation the separation of macromolecular and particulate species is achieved by injecting a small sample containing the species into a stream of carrier fluid that flows lengthwise through a thin elongated channel. The primary driving force, generated by an externally controlled field or gradient, is applied transversely across the thin dimension of the channel in a direction perpendicular to flow. This driving force induces a transverse displacement of component species across the channel, generally toward one wall termed the accumulation wall. The present invention relates to apparatus and procedures wherein the driving force is an electrical field.

As the particles approach the wall, their overall motion is eventually halted by one of several possible opposing forces or displacement effects. The particles may diffuse back away from the wall. They may also be repelled from the wall by various repulsive forces. Because there opposing influences bring the initial field-driven transport to a halt, each type of particle (or macromolecule) comes rapidly to equilibrium in the channel. The final equilibrium position or steady state distribution across the thin dimension of the channel is determined by the balance of the primary driving force and the opposing forces. Different kinds or sizes of particles are subject to different forces and thus have different equilibrium positions or steady state distributions.

As the stream of carrier fluid flows through the channel, it carries the various particle types along with it. Most often the channel flow profile is parabolic or near-parabolic, which means that the velocity of flow is highest in the center of the channel midway between the channel walls, and slowest near the walls. With parabolic flow, any particle type whose equilibrium position is near a wall is carried only slowly down the channel by flow. A particle type whose steady state position is further removed from the nearest wall is displaced more rapidly by flow. Because flow displacement ("migration") velocities vary in this manner from one particle type to another, the different particle species are separated.

In accordance with the present invention improved apparatus is disclosed for performing electrical field-flow fractionation. As illustrated in the drawings, the apparatus comprises a thin flow channel 10 having a top wall 12, a bottom wall 14, two side walls 16, an inlet end 18 possessing an inlet means and an outlet end 20 possessing outlet means. The top wall 12 and bottom wall 14 are in all instances formed such that at least the inner surfaces of each of the top and bottom wall 12 and 14 that face the flow channel 10 are made of an electrically conductive material such that the inner surfaces of the top and bottom walls 12 and 14 form electrodes as well as boundary surfaces of the flow channel 10.

In the embodiment of the apparatus shown in FIG. 1, the top and bottom walls 12 and 14 are each formed from electrically conductive graphite material. In a specific example of the apparatus as shown in FIG. 1, a 158 micron thick mylar spacer 22 is sandwiched in between two epoxide-cured and highly polished graphite slabs which form the top and bottom walls 12 and 14. Plexiglass sheets 50 hold the sandwiched members together. The plexiglass sheets are in turn held together by bolts spaced apart by about 2 inches.

The interior portion of the mylar spacer 22 is cut out such that the forward end of the spacer 22 forms the forward wall 18 of the flow channel 10, and the rearward end of the spacer 22 forms the rear wall 20 of the flow channel 10. The two sides of the mylar spacer 22 form the opposite, elongate thin sides 16 of the flow channel 10. The length of the channel 10 is considerably larger than the breadth of the channel. In a specific example, the length of the channel 10 is 89 cm while the breadth of the channel 10 is 2 cm.

Figure 2:
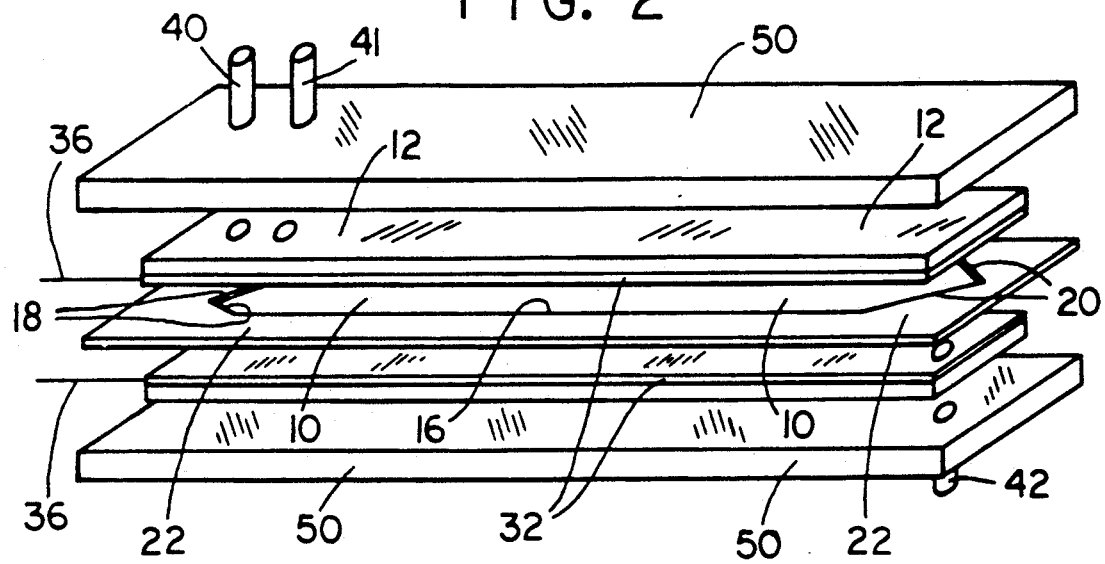

A somewhat modified embodiment of apparatus of the present invention is shown in FIG. 2 wherein the top and bottom walls 12 and 14 are made of a rigid material that is not necessarily electrically conductive, a material such as glass for example. At least the inner surfaces of the top and bottom walls 12 and 14 of the apparatus shown in FIG. 2 are made from an electrically conductive gold coating formed as a layer 32 on the surfaces of the walls 12 and 14. In a preferred embodiment of the apparatus shown in FIG. 2, the walls 12 and 14 are made of glass, with a layer 32 of gold coated on the inner surfaces of the glass. The mylar spacer 22 and the other components of the apparatus shown in FIG. 2 are essentially identical with the components of the apparatus of FIG. 1 that are described both hereinbefore and hereinafter and referred to with similar reference numerals.

Means are provided for applying a voltage differential to the electrically conductive inner surfaces of the top and bottom walls 12 and 14. As illustrated in the drawings, electrical leads 36 are advantageously provided leading from the electrically conductive walls 12 and 14 or from the electrically conductive layer 32 on the walls 12 and 14. The leads 36 can be attached to a voltage source such as a battery or other source of D.C. voltage. In the embodiment of the apparatus shown in FIG. 2, the applied potential can drop along the thin conductive layers 32 in the longitudinal downstream direction of the channel 10. This drop in potential along the length of the conductive layers 32 can be avoided by having the connecting leads 36 comprise strips of copper metal applied along one entire longitudinal side of the conductive layers 32 of the walls 12 and 14.

A carrier fluid flows through the channel 10. In a preferred embodiment, the carrier is delivered by a metering pump. The carrier fluid is introduced through an influx port 40 positioned at the upstream end of the flow channel 10, and an effluent port 42 is positioned at the downstream end of the flow channel 10. The influx port 40 and effluent port 42 can be positioned in opposite channel walls 12 and 14 as is shown in the drawings, or both ports 40 and 42 can be positioned or located in any one of either of the walls 12 and 14. As is well known in the art, the fluid flowing through the flow channel 10 near the downstream end thereof is monitored by a detector (not shown in the drawings). Test samples containing particles that are to be resolved and separated are injected into the carrier fluid at or near the upstream end of the flow channel 10. The injection is made through an injection port, which may be part of the influx port 40, or as shown in the drawings be an independent port 41 located downstream from the influx port 40. The detector detects the separated particles as they exit the channel 10 near the downstream end of the channel 10.

In one embodiment of the invention, the carrier fluid can be essentially deionized or distilled water. In a particularly preferred embodiment of the invention, the carrier fluid comprises water containing a red-ox couple that carries current while simultaneously reducing polarization products that would otherwise form at the electrically conductive inner surfaces of the top and bottom walls 12 and 14. Preferably, the red-ox couple is present in a dilute concentration of between about 0.001 and 0.005 moles per liter. In a preferred embodiment, the red-ox couple is quinone/hydroquinone.

In a preferred mode of operation of the apparatus shown in the drawings, the channel 10 is maintained in a vertical orientation, with the influx port 40 located at the bottom end of the apparatus. When operated in the vertical orientation, gravitational effects are not coupled with the electric field, and sample accumulation may equally well occur at either electrode. However, the apparatus can be operated in the horizontal mode when gravitational effects are desired to augment or detract from the electrical field. When operating in the horizontal orientation, a simple switch in electrode polarity changes the retention of particles in the steric range from a high level seen when the electrical and gravitational fields are applied in unison to augment each other, to weak or negligeable levels when the electrical and gravitational fields oppose each other.

An example will now be described of the process for resolution and separation of particles in a test sample using an electrical field-flow fractionation apparatus similar to those shown in the drawings. A thin flow channel 10 having a top wall 12, a bottom wall 14, two side walls 16 and an inlet end 18 possessing an inlet means and an outlet end 20 possessing an outlet means are formed as shown in the drawings. In this example, the apparatus is oriented with the flow channel 10 being vertical. The inner surfaces of the top and bottom walls 12 and 14 are made to be electrically conductive as explained hereinabove so that the inner surfaces of the top and bottom walls 12 and 14 form electrodes as well as boundary surfaces of the channel 10.

In the apparatus of this example, a 158 micron thick mylar spacer 20 was sandwiched in between two epoxide-cured and highly polished graphite blocks which formed the top and bottom walls 12 and 14. The system was held together with sheets 50 of plexiglass that were bolted together to hold the sandwiched materials firmly in place. A voltage differential was applied across the electrodes forming the inner surfaces of the top and bottom walls 12 and 14 of the channel 10.

A carrier fluid was introduced through the inlet port 40 to flow through the channel 10. Two different carrier fluids were tested. A control test used a conventional 0.01M aqueous solution of Tris-HCl having a pH of 7.4. In a separate set of test runs, the carrier fluid was a dilute aqueous solution containing the a red-ox couple quinone/hydroquinone. The particular carrier fluid used in these latter runs was 0.002M quinone/hydroquinone having a pH of 5.9. In all tests, the carrier fluid was pumped into the inlet port 40 to maintain a channel flow rate of one mL per minute.

A test sample containing polystyrene latex particles was injected into the liquid carrier stream through an injection port that was integral with the influx port 40 near the upstream end of the flow channel 10, and the effluent was monitored near the outlet end of the flow channel 10 by a UV detector operating with a 254 nm light source.

In the control test run using the conventional Tris-HCl carrier, immediately upon application of the potential (1.5 volts) across the electrodes of the channel 10, the initial high current dropped to and remained at an insignificant level even with carrier fluid maintained under constant flow. Under such conditions, the electrical field applied across the channel 10 was minimal and insufficient to achieve any resolution and separation of the test particles injected into the carrier fluid.

By contrast, the same potential applied across the electrodes in the test runs in which the carrier fluid was the quinone/hydroquinone solution produced a current which remains high indefinitely under conditions of flow through the channel. Polarization at the electrodes is significantly reduced, and the resulting electrical field applied across the channel 10 resulted in excellent resolution and separation of the test particles injected into the carrier fluid. Similarly, when the 1.5 volt potential difference was applied across the channel with the carrier fluid consisting of deionized water, a stable current was observed although at a weaker level than in the case of the carrier fluid containing quinone/hydroquinone. The particles of the test samples were well resolved according to their size whether the carrier fluid was deionized water or water containing quinone/hydroquinone.

The range of particle sizes which can be resolved and separated in the present system is large, spanning both the normal and steric modes of operation. Polystyrene latex particles carry a negative charge in aqueous media, and under an applied potential of as little as 0.32 volt, significant retention has been observed for particles ranging in size from 69 nm to 10 microns.

Although preferred embodiments of the improved field flow fractionation processes of the present invention have been illustrated and described, it is to be understood that the present disclosure is made by way of example and that various other embodiments are possible without departing from the subject matter coming within the scope of the following claims, which subject matter is regarded as the invention.

We claim:

1. A process for resolution and separation of particles in a test sample using an electrical field-flow fractionation channel through which a carrier fluid flows in a flow profile that is substantially parabolic generally throughout the channel, said process comprising;

forming a thin flow channel having a top wall, a bottom wall, two side walls and an inlet end possessing an inlet means and an outlet end possessing an outlet means, with the top wall and bottom wall being spaced from each other by no more than about 200 microns;

forming the inner surfaces of the top and bottom walls so that they are electrically conductive, whereby the inner surfaces of the top and bottom walls form electrodes as well as the opposite, broad boundary surfaces of said channel;

applying a voltage differential to the electrodes forming the inner surfaces of the top and bottom walls of said channel;

introducing the carrier fluid through said inlet means to flow through said channel and out of said outlet means, said carrier fluid comprising deionized or distilled water that contains a red-ox couple for carrying current in the carrier fluid in said channel;

injecting the test sample into the carrier fluid flowing through the channel; and monitoring the carrier fluid at a downstream location from the injecting for particles from the test sample.

2. A process in accordance with claim 1 wherein the red-ox couple is present in a dilute concentration of between about 0.001 and 0.005 moles per liter of carrier fluid.

3. A process in accordance with claim 2 wherein the red-ox couple is quinone/hydroquinone.

4. A process in accordance with claim 1 wherein the top and bottom wall are made from electrically conductive graphite material.

5. A process in accordance with claim 1 wherein the red-ox couple is quinone/hydroquinone.

6. A process in accordance with claim 1 wherein the top and bottom wall are made of glass having electrically conductive gold coating forming at least the inner surfaces of said top and bottom walls.

7. A process in accordance with claim 6 wherein said carrier fluid contains a red-ox couple present in a dilute concentration of between about 0.001 and 0.005 moles per liter of carrier fluid.

8. A process in accordance with claim 7 wherein the red-ox couple is quinone/hydroquinone.

* * * * *